United States Patent [19]

Weissman

[11] Patent Number: 4,990,088

[45] Date of Patent: Feb. 5, 1991

[54] DENTAL TOOL COMBINING REAMER AND ROUTER

[76] Inventor: Bernard B. Weissman, 225 E. 48th St., New York, N.Y. 10017

[21] Appl. No.: 172,483

[22] Filed: Mar. 24, 1988

[51] Int. Cl.[5] .............................................. A61C 3/02
[52] U.S. Cl. ..................................... 433/165; 433/102
[58] Field of Search ................. 433/102, 165, 166, 81, 433/224

[56] References Cited

U.S. PATENT DOCUMENTS

| | | | |
|---|---|---|---|
| 1,200,921 | 10/1916 | Chester | 433/165 |
| 2,453,696 | 11/1948 | Brooks | 433/102 X |
| 3,894,339 | 7/1975 | Manzi | 433/166 |
| 4,019,254 | 4/1977 | Malmin | 433/102 |
| 4,270,903 | 6/1981 | Nash | 433/165 |
| 4,389,192 | 6/1983 | Neuwirth | 433/166 |
| 4,457,710 | 7/1984 | McSpadden | 433/81 |
| 4,661,061 | 4/1987 | Martin | 433/102 |
| 4,758,156 | 7/1988 | Johnson | 433/81 |

FOREIGN PATENT DOCUMENTS 2524105  2/1976  Fed. Rep. of Germany ...... 433/102
 291668  6/1953  Switzerland ........................ 433/165

Primary Examiner—Robert P. Swiatek
Assistant Examiner—Nicholas D. Lucchesi
Attorney, Agent, or Firm—Paul J. Sutton; Barry G. Magidoff; Anthony Amaral, Jr.

[57] ABSTRACT

There is provided a combination dental tool for boring and grinding undercut bore holes in teeth. The tool includes a boring end portion tapering longitudinally endwardly to a minimum effective diameter at the tip and providing an axially facing cutting surface for drilling a bore into a tooth upon rotation of the tool. A shank portion extending axially from the drilling end portion includes at least two successive longitudinally extending sections, the first section having laterally facing cutting surfaces and a relatively larger effective diameter, and the second section, immediately adjacent the first section, having a relatively smaller diameter. Using this tool, an axially directed force forms the bore hole, and a laterally directed force exerted on the tool within a previously drilled bore hole, routs out an undercut portion in the internal surface of the bore.

12 Claims, 4 Drawing Sheets

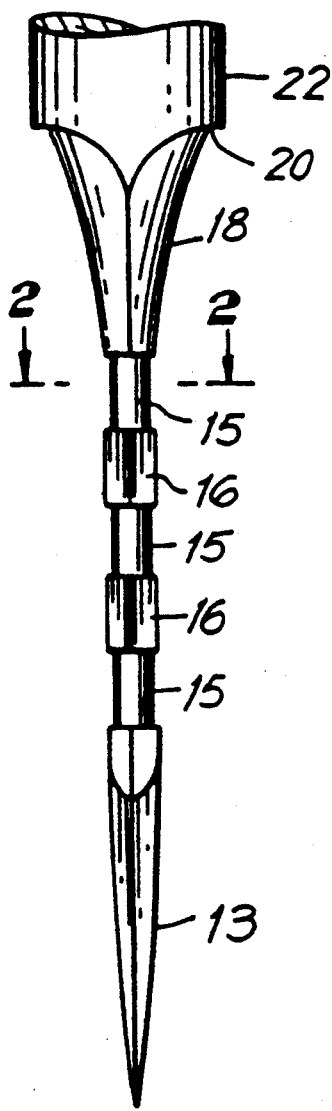
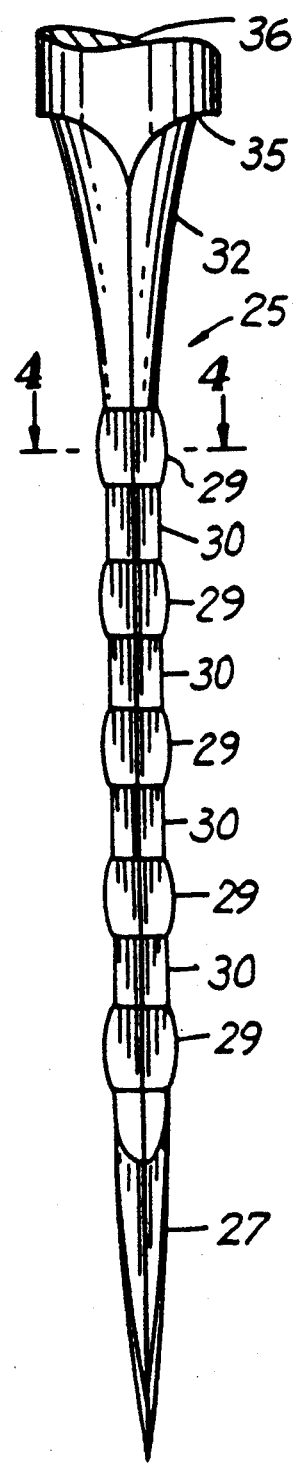
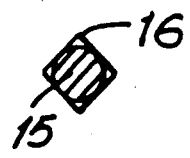

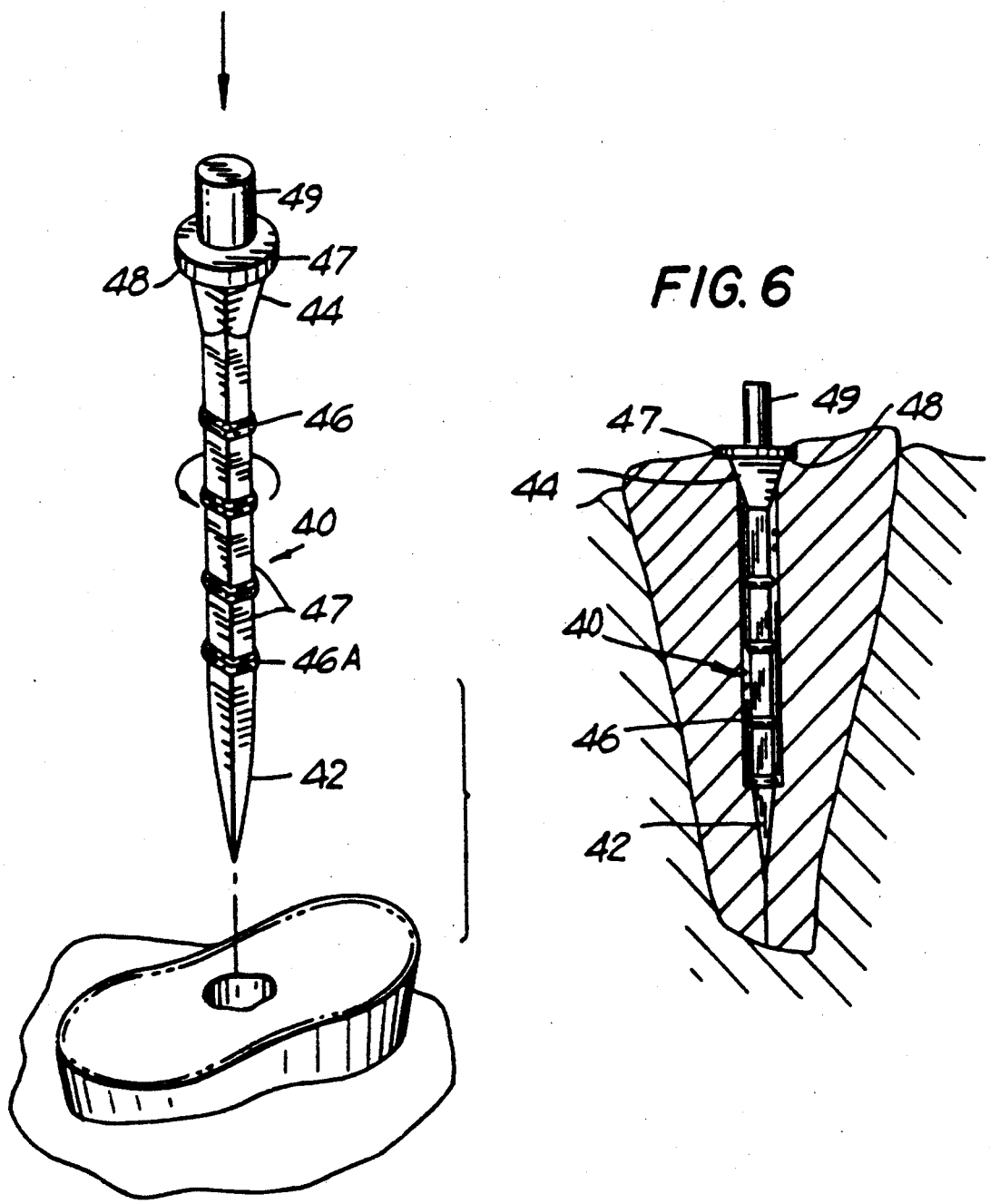

DENTAL TOOL COMBINING REAMER AND ROUTER

BACKGROUND OF THE INVENTION

The present invention relates to a tool for use in dentistry, and more particularly to a dental tool which provides for the drilling of a bore hole and for the forming of lateral undercuts along the interior longitudinal surface of the bore hole and which can be rotated by a dental handpiece associated with a dental drill.

It is well known in the dental field to provide a drill tool bit for forming a bore hole through the root canal of a tooth. It is also common to grind away the upper surface of the tooth, using a dental grinding tool to provide space for a dental prosthetic to be anchored to the tooth via an anchor extending into and cemented within the bored out root canal. Such dental anchors are generally cemented into the bore hole and in some cases the anchors are provided with undulating lateral surfaces to further assist in securing the anchor to the cement. It has been found, however, that the security of the dental prosthetic may be compromised by a failure of the cement holding the anchor in the bore, as well as by the difficulty of seating the prosthetic around a projecting portion of the anchor and onto the top of the tooth.

SUMMARY OF THE INVENTION

Accordingly, it is an object of the present invention to provide a dental tool which combines the effectiveness of a bore drill and an undercutting routing tool to improve the security of a cemented anchor in and to the tooth. It is a further object of the present invention to optimally provide a counterboring portion to enlarge the outer end of the bore and a platform grinding portion to provide a reference platform substantially perpendicular to the bore at the top surface of the tooth. It is a further object of the present invention to provide all of these effects on a single tool, thus permitting not only efficiency in the number of tools required, but also simplifying the problem of maintaining the integrity of and desired mutual relationships between the bore hole, a flat platform on the tooth, and the cemented anchor in the bore hole.

These and other objects are achieved in accordance with the present invention wherein the dental tool includes a first holder end portion designed to be receivable in a dental tool holder, such that the dental tool holder can rotate the dental tool; a second drilling end portion tapering longitudinally endwardly to a minimum effective diameter at the second end and providing an axially facing drill cutting surface for drilling a bore into a tooth of a patient upon rotation of the tool; a shank portion extending between the two end portions and including at least two alternating longitudinally extending sections, the first shank section having laterally facing cutting surfaces and a relatively larger effective diameter, and the second shank section having a smaller effective diameter such that the application of laterally directed force to the tool while the tool is being rotated within the bore of the tooth provides for the routing out of notches, or undercut surfaces, along the interior of the bore in the direction of the lateral force. The first holder end portion of the too is designed to be removably secured to a conventional dental handpiece so as to be rotatably driven from the handpiece. The tool is to be secured into the handpiece such that it will maintain its position upon the application of longitudinal force exerted toward the second drilling end of the tool and upon the exertion of lateral force while the tool is being rotated. There is further preferably provided, at a portion intermediate the shank portion and the first holder end, a divergent counterbore drilling section capable of forming an enlarged bore diameter at the outer end of a bore hole. Most preferably, there is also provided a substantially planar, annular grinding surface surrounding and immediately adjacent to the maximum diameter of the counterbore portion for forming a flat platform on a tooth upper surface, surrounding the bore.

The combination dental tool of the present invention is to be used with a conventional dental tool handpiece as providing support and driving power for the device. As used, the drill point, or reamer, is placed within the root canal opening of a tooth stub. The stub has previously been ground down to approximately the desired height above the gum line by removing broken or decayed dental material. The combined tool is held by a conventional dental handpiece and the power applied to rotate the tool in a conventional manner, pressing downwardly against the tooth to bore out a hole of the desired depth.

It is well known in the dental field to select a drill, or reamer, of a proper length and diameter to obtain the desired size bore hole. For the present invention, however, the length of the tool must be carefully calibrated with the desired depth of the bore, as the tool must be inserted substantially completely into the bore hole such that the upper portion of the tool forms a funnel-shaped enlargement of the entrance to the bore hole, by reaming out a counterbore. In addition, the platform grinding tool must reach at least the top surface of the tooth to form a flat platform surrounding the bore, preferably extending a certain distance below the surface of the surrounding tooth material.

After a hole is bored to the desired depth, using the tool of the present invention, the tool is withdrawn a short distance above the bottomed out position, and lateral pressure exerted by the tool on the sides of the bore alternately in the facial and lingual directions. In this manner, the enlarged first shank sections rout out laterally undercut notches at the spaced positions of such first sections along the bore, preferably in the lingual and facial directions. Simultaneously with the formation of the undercut notches along the bore, the counterbore reaming portion at the top of the bore hole acts against the facial and lingual sides of the entrance to the bore, and the planar grinding surface acts on the tooth surface, forming an enlarged ellipsoid outer opening to the bore, and an ellipsoid flat platform around the outer opening to the bore in the tooth perpendicular to the central axis of the bore.

An anchor post for a dental prosthesis ca then be inserted into the bore hole; an improved anchor post can be used, having an enlarged portion with an ellipsoid cross-section, shaped and sized so as to fit within the ellipsoid counterbore portion of the bore. Such an anchor post is not susceptible to rotation and is strengthened at a critical location. The portion of the anchor post extending deeper into the bore hole can be cylindrical, as it is noted that the tool does not elongate the cross-section of the entire inner bore, only those portions contacted by the cutting surfaces of the first sections of the shank portion.

Further details of the present invention are shown in the accompanying drawings, by way of example and not by way of exclusion. Many portions of the invention or the context therefor are shown in schematic representation, where greater detail is unnecessary as it will be apparent or well-known to those skilled in the art. Referring to the accompanying drawings:

FIG. 1 is a side elevation view of one embodiment of the present invention;

FIG. 2 is a cross-section view along line 2—2 of FIG. 1;

FIG. 3 is a side elevation view of a second, and longer, embodiment of the present invention;

FIG. 4 is a cross-sectional view of the embodiment of FIG. 3 taken along lines 4—4;

FIG. 5 is a perspective view showing a tool of the present invention above a tooth stub;

FIG. 6 is a cross-section elevation view showing a tool of the present invention fully deployed within the bore of the tooth stub;

Figure 7:
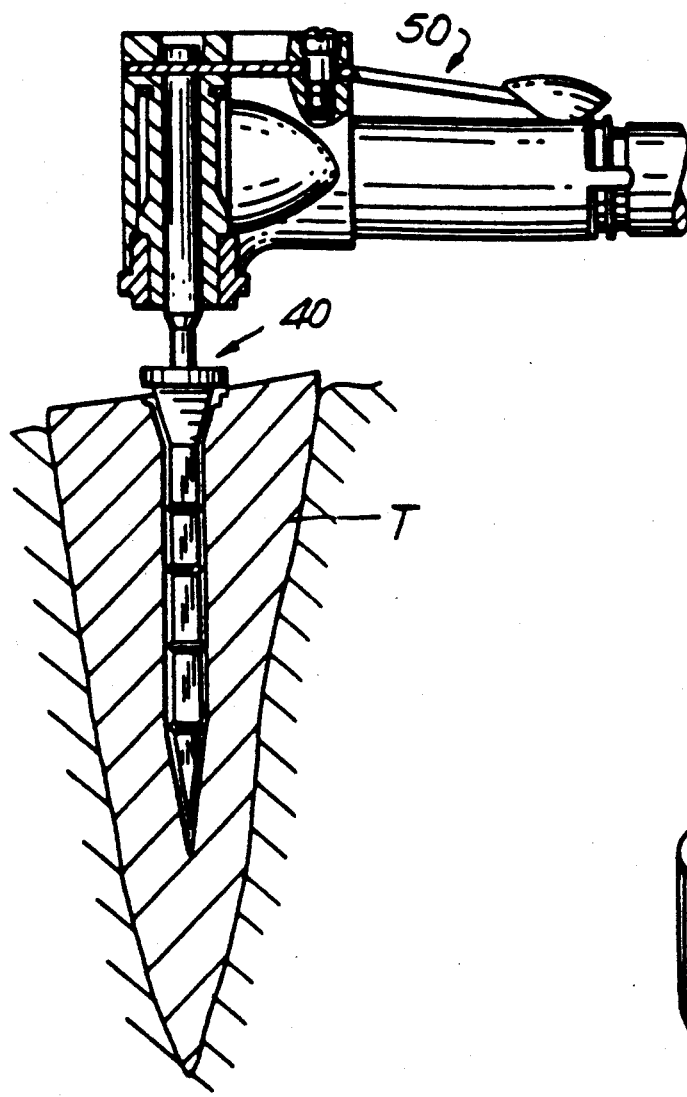
FIG. 7 is a side elevation view, in partial cross-section, of a tool of the present invention held by a conventional dental handpiece in the first stage of the routing procedure of the present invention.

Referring to the drawings, a relatively short combination tool indicated by the numeral 11 is shown having a reaming, or drilling, first pointed end 13, a first shank cutting section 16 and second, minor diameter shank sections 15. Located immediately adjacent the uppermost second section 15 is the divergent counterbore section 18. Surrounding the maximum diameter of the counterbore section 18 is an annular planar grinding surface 20, and immediately thereabove a top cutting section 21 extending a relatively short distance above the grinding surface 20. A holder end portion 22 extends outwardly from the grinding surface 20. The upper section of the holder portion 22 is not shown but is of conventional design suitable for being secured to conventional dental handpieces, and the connecting portions should be adapted for whichever dental handpiece is to be used. The cross-sections of the cutting sections 13, 16, 18 and 21 are preferably substantially square and the cross-section of the minor diameter intermediate sections 15 is round.

An alternative form of the combination tool of the present invention, generally indicated by the numeral 25, is shown in FIG. 3, in this embodiment of relatively greater length. However, the relative lengths are not a function of the other differences between the embodiments of FIGS. 1 and 3.

The cutting portions of the tool 25 of FIG. 3, include the lower drilling end 27, the counterbore portion 32, the larger routing sections 29, and the top cutting section 37. The second, minor diameter, shank sections 30 do not include a lateral cutting surface, such as is present on the first shank sections 29. Immediately adjacent the maximum diameter of the counterbore portion 32 is the annular planar grinding surface 35 and top cutting section 37, immediately below the broken away holder end 36. The planar grinding surface 35 also can be coated, with a hard, fine granular substance, such as diamond dust. The cross-sectional view of FIG. 4 shows that both the routing sections 29 and the intermediate, minor diameter, sections 30 are substantially square in cross-section.

The tool can be formed having a cross-section of various regular polygons as desired, the apices of the polygons in the routing sections 29 providing the cutting edges. When the term "diameter" is used for such polygonal cross-sections, it refers to the "effective diameter", i.e., the diameter of a bore hole cut by such sections rotating about a single axis.

The embodiment of FIGS. 3 and 4 provide laterally cutting routing sections 29 having an outer surface forming a substantially continuous curve between two smaller diameter intermediate sections 30. The curved cutting surfaces of the first sections 29 can be optionally coated with hard, fine granular material, such as diamond dust, if desired.

Referring to FIGS. 5 through 8, yet another embodiment of the combination dental tool of the present invention is shown. In this embodiment, the cutting router sections 46 are of somewhat smaller longitudinal dimension than the intermediate, minor diameter sections 47, of the shank portion. Both shank sections 46, 47, as well as the drilling end portion 42, the counterbore portion 44 and the top cutting section 47, have substantially square lateral cross-sections. The initial reaming out of the tooth root canal is carried out not only by the end drilling portion 42 but by the leading routing ring section 46a. The annular planar grinding surface 48 extends radially outwardly from the maximum diameter of the counterbore 44, inside of the holder section 49, and perpendicular to the axis of the shank sections 46, 47.

Referring to FIG. 7, wherein the tool of the present invention is located within a bored hole, the tool, generally indicated by the numeral 40, is operatively supported and held by a conventional handpiece, generally indicated by the numeral 50. The handpiece is of a conventional type, which can provide support and carry the driving power to the tool 40 to cause it to rotate. The handpiece 50 can securely hold and mechanically drive the tool 40, while being subjected to longitudinal force axially into the tooth, during a reaming out operation, or while being subjected to force applied laterally, and against the lateral interior surfaces of the bore. Such hand tools are well-known, and can, e.g., be air or motor driven, or directly gear driven, by straight or right angle dental rotary devices.

In carrying out the procedure in accordance with the present invention, after the bore is fully formed in the tooth, as shown by FIG. 6, wherein a flat platform surface has also been formed surrounding the bore and below the top surface of the tooth, the tool 40 is lifted above its bottommost position, as shown in FIG. 7, such that the annular grinding surface 48 is at or just below the top surface of the tooth. Lateral pressure is exerted from the handpiece through the tool and against the inside of the tooth bore, while the tool is continuously rotated at a high speed. Such pressure is preferably exerted successively in the lingual and facial directions, such that the grinding rings 46 are forced against the sides of the bore, routing out undercut surfaces, or notches, along the length of the bore in those directions. The pressure is exerted first in one of the directions and then in the other of the lingual and facial directions. As the undercuts are formed in the bore, the counterbore portion 44 and the top cutting surface 47 of the tool at the upper surface of the bore hole and the annular planar grinding surface are also elongating the upper portion of the bore and the outer platform, respectively, each to a substantially oval or ellipsoid cross-section. The routing rings 46 (or 29 or 16) are preferably approximately 25% larger in diameter than the second, minor diameter sections 47 (or 30 or 15), such that upon fully routing the undercut notches, the notches have a diameter approximately 50% greater than the original bore hole. The counterbore portion is also extended an equal amount to form the oval portion.

Figure 11:
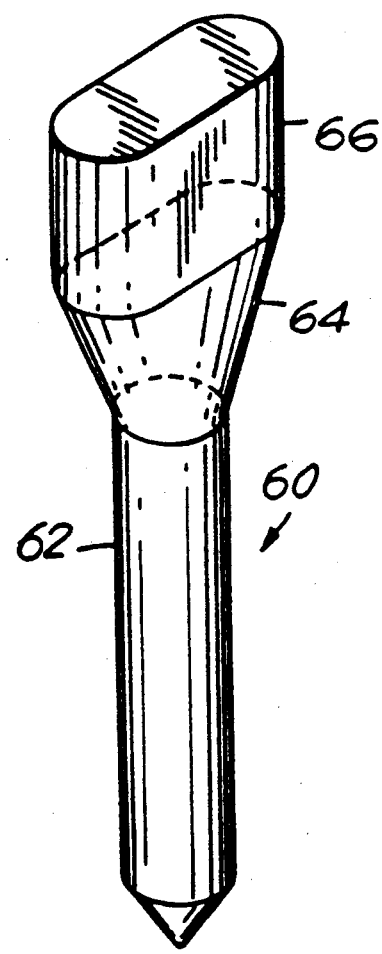
FIG. 11 is an isometric drawing of a dental anchor post having an oval top section for insertion into the reamed and routed tooth bore formed in accordance with the present invention.
Figure 8:
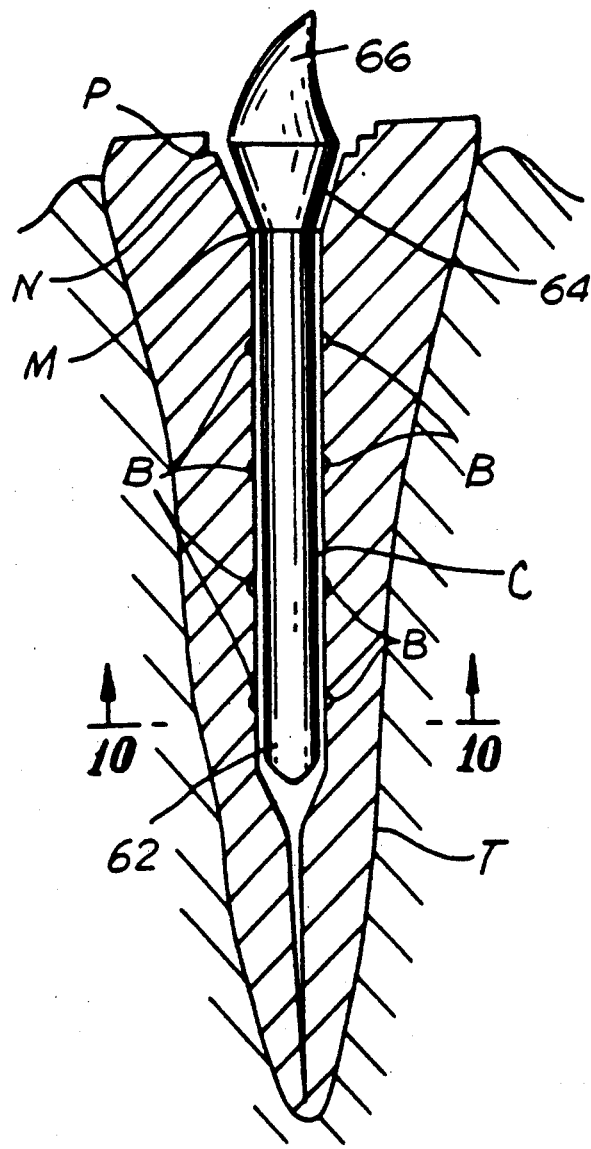
FIG. 8 is an elevation cross-section view of the dental tool of the present invention in a fully reamed and routed bore of a tooth (shown in cross-section) in accordance with the present invention.
Figure 9:
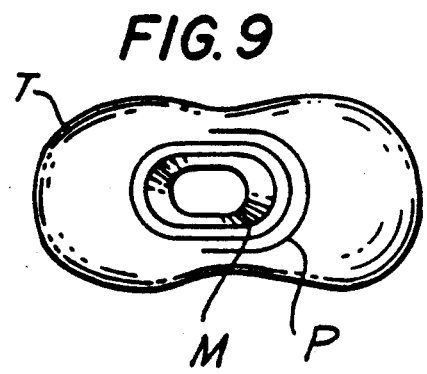
FIG. 9 is a top view of the reamed and routed tooth of FIG. 8 showing the oval counterbore portion and flat platform.
Figure 10:
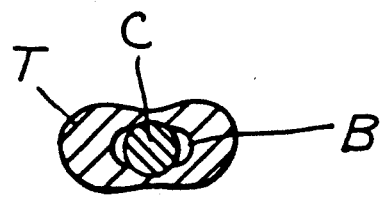
FIG. 10 is a cross-section view taken along lines 10—10 of FIG. 8.

A fully reamed and routed tooth stub, into which a suitable anchor post, has been inserted is shown in FIGS. 8 to 10; the anchor post is shown in FIG. 11. An anchor post, generally indicated by the numeral 10, is inserted into the prepared bore hole. The anchor post comprises an interior shaft portion 62, of a generally circular cross-section, extending from a divergent base member 64 having a generally ellipsoidal cross-section, dimensioned to fit within the elongated counterbore in the tooth. Extending outwardly from the divergent base member 64, is the anchor post core 66, for securing to a tooth prosthesis. Although the particular shape of the anchor post core 66 is not a feature of this invention, the enlarged base member 64 permits the providing of a larger anchor post core 66. This, in turn, permits the dentist to sculpt the core to provide the desired prosthetic core for each patient, in accordance with requirements well known to dentists skilled in the art.

For example, the large core can be sculpted (as by grinding, filing or cutting) in the dentists office, to the shape shown in FIG. 8. The jacket, or restoration cap, can then be applied by the dentist over the sculpted core 66 in the office without requiring additional laboratory casting and molding procedures. Thus, using the system of the present invention, in one visit to a dentist's office, the post can be cemented into the tooth stub and the core sculpted to the desired shape. The impression for the cap can then be taken directly.

It is understood that the core 66 need not be made of the same material as the rest of the anchor post 60, 64 (which is inserted into the tooth bore), although the anchor post including the core is to be provided to the dentist as an integral product. For example, titanium alloy is the material of choice for that portion of a prosthesis to be inserted into the tooth bore. The core 66, however, should be of a softer more easily sculpted material such as a low grade gold alloy, a ceramic dental material, polymer composite, or a ceramic/metal or polymer/metal laminate, for example. The laminates are especially useful when the nonmetallic component is of a light color which will not create a "shadow" through the cap and is to be on the exterior side of the tooth cap. All of these materials, as well as other materials well-known to the art, can be joined to the base portion by well-known means, such as welding, soldering, or casting or molding together.

Referring, by way of example to the dental tool of FIG. 3, the diameter of the enlarged, routing cutting sections 29 is generally in the range 0.03 inch to about 0.08 inch, e.g., approximately 0.06 inch. The minor diameter intermediate sections 30 have a diameter of approximately fifty percent of the routing sections 29, e.g., 0.03 inch. The maximum diameter of the counterbore portion 32 is about fifty percent greater than that of the routing sections, e.g., 0.09 inch, and the outer diameter of the annular planar grinding surface 35 is about thirty percent to about fifty percent again larger, e.g. 0.12 inch. The tool can be formed of stainless steel, or other hard material, and coated with a fine granular abrasive, e.g., diamond dust, if desired.

THE PATENTABLE EMBODIMENTS OF THE INVENTION WHICH ARE CLAIMED ARE AS FOLLOWS:

1. A combination dental tool providing for drilling and grinding, the tool comprising a first holder end portion designed to be receivable in a dental tool holder such that the dental holder can rotate the dental tool; a second drilling end portion having a proximal end and a distal tip end relative to the holder end portion, the drilling end tapering longitudinally from a maximum effective diameter at the proximal end to a minimum effective diameter at the distal tip end, the drilling end portion having a polygonal cross-section, which provides axially facing cutting edges for drilling a bore into a tooth of a patient upon rotation of the tool; a shank portion extending intermediate the two end portions and including a first and a second intersecting, longitudinally extending, axially successive shank sections, the first such shank section having laterally facing cutting edges, a relatively larger effective diameter, and a polygonal cross-section; and the second such shank section having a relatively smaller diameter relative to the first shank section and to the maximum diameter of the drilling end portion; the intersection of the first and second shank sections of the tool being at angles not less than a right angle; such that upon the application of a laterally directed force, while rotating the tool within a previously drilled bore, undercut portions are routed out from the interior surface of the bore.

2. The combination dental tool of claim 1 wherein the second shank section is at least as long, in an axial direction, as the first shank section.

3. The combination dental tool in accordance with claim 1, further comprising a divergent counterbore cutting portion having counterbore cutting surfaces of continuously increasing diameter, and extending from adjacent the shank portion towards the holder end, the counterbore cutting surface diameter increasing to a maximum towards the holder end.

4. The combination dental tool of claim 3 further comprising a substantially planar, annular platform grinding surface extending radially outwardly and facing towards the drilling end of the tool, the inner edge of the annular platform grinding surface being adjacent the maximum diameter of the counterbore cutting portion.

5. The combination tool of claim 2, wherein the annular grinding surface is substantially perpendicular to the axis of the shank portion.

6. The combination dental tool of claim 3 wherein the shape of the lateral cross-section of the counterbore portion is a square.

7. The combination dental tool of claim 1 wherein the maximum effective diameter of the drilling end portion is substantially equal to that of the first shank section.

8. The combination dental tool of claim 1 wherein the lateral cutting surfaces are grinding surfaces coated with relatively hard and fine granular material.

9. The combination dental tool of claim 1 wherein the shape of the lateral cross-section of the first shank section is a square.

10. A combination dental tool providing for drilling and grinding, the tool comprising a first holder end portion designed to be receivable in a dental tool holder such that the dental holder can rotate the dental tool; a second drilling end portion having a proximal end and a distal tip end relative to the holder end portion, the drilling end tapering longitudinally endwardly from a maximum diameter at the proximal end to a minimum effective diameter at the distal tip end, the drilling end portion having a polygonal cross-section and which provides axially facing cutting edges for drilling a bore into a tooth of a patient upon rotation of the tool; a shank portion extending intermediate the two end portions and including a first and a second axially successive, longitudinally extending shank sections; the first such shank section having laterally facing cutting surfaces and a relatively larger effective diameter, the laterally facing cutting surfaces of the first shank section being defined by a substantially continuous curve, extending axially from the intersection with the second shank section; and the second shank section having a relatively smaller diameter relative to the first shank section and to the maximum diameter of the drilling end portion, such that upon the application of a laterally directed force while rotating the tool within a previously drilled bore, undercut portions are routed out from the interior surface of the bore.

11. The combination dental tool of claim 10 wherein the shape of the lateral cross-section of the second shank section is substantially circular.

12. The combination dental tool of claim 10 wherein the shape of the lateral cross-section of the first shank section is an equilateral polygon.

* * * * *